(12) United States Patent
Burger et al.

(10) Patent No.: US 6,506,285 B1
(45) Date of Patent: Jan. 14, 2003

(54) SYNTHESES OF 5,5'-DIFORMYL-2-2'DIFURAN AND DERIVATIVES THEREOF

(75) Inventors: Gregory James Burger, Zwa Zulu Natal (ZA); Alan Douglas Wills, Zwa Zulu Natal (ZA)

(73) Assignee: Illovo Sugar Limited, Durban (ZA)

( * ) Notice: Subject to any disclaimer, the term of this patent is extended or adjusted under 35 U.S.C. 154(b) by 0 days.

(21) Appl. No.: 09/554,433
(22) PCT Filed: Sep. 15, 1999
(86) PCT No.: PCT/ZA99/00087
§ 371 (c)(1), (2), (4) Date: Jul. 17, 2000
(87) PCT Pub. No.: WO00/15623
PCT Pub. Date: Mar. 23, 2000

(30) Foreign Application Priority Data

Sep. 15, 1998 (ZA) .............................................. 98/8414

(51) Int. Cl.[7] ............................................. C07D 309/00
(52) U.S. Cl. ................................................. 204/157.69
(58) Field of Search ................... 204/157.69; 422/186.3

(56) References Cited

U.S. PATENT DOCUMENTS 4,229,202 A * 10/1980 Mullerheim et al. ............. 71/8

OTHER PUBLICATIONS

Tymyanskii et al., "Photodimerization of Furfural Bromo Derivatives", Zh. Org. Khim., vol. 24, No. 2, pp. 459–460. (month unavailable, 1988).*
Itahara, T., "Arylation of Aromatic Heterocycles with Arenes and Palladium(II) Acetate", J. Org. Chem., vol. 50, pp. 5272–5275. (month unavailable, 1985).*
Markl et al., "Zur Molekuldynamik Isomerer Antiaromatischer [28]Tetraoxaporphyrinogene (6.0.6.0)–Isomer [26]Tetraoxaporphyrin (6.0.6.0) Dikationen", Tetrahedron, vol. 52, No. 36, pp. 11763–11782. (month unavailable, 1996).*

* cited by examiner

Primary Examiner—Edna Wong
(74) Attorney, Agent, or Firm—Young & Thompson

(57) ABSTRACT

A method of synthesizing 5,5'-diformyl-2,2'-difuran and derivatives thereof, including the steps of subjecting a reaction mixture of furfural or a derivative thereof to photochemical irradiation with a halogenated furfural in the presence of an acid scavenger and then harvesting the produced 5,5'-diformyl-2,2'-difuran and derivatives.

8 Claims, 1 Drawing Sheet

SYNTHESES OF 5,5'-DIFORMYL-2-2'DIFURAN AND DERIVATIVES THEREOF

TECHNICAL FIELD OF THE INVENTION

This invention relates to the synthesis of 5,5'-diformyl-2,2'-difuran and derivatives thereof, as well as to the derivatives themselves as new chemical compounds.

BACKGROUND OF THE INVENTION

Difunctional aromatic monomers have vast potential and uses in the polymer industry and are presently used in many applications. Present technology to produce difunctional monomers through two base nuclei from the single nucleus has been achieved utilising a metal halide intermediate. This technology has the disadvantage of requiring an initial halogenation step after which the halogenated nuclei are treated with a metal powder. High temperatures, long reaction time and laborious work-up procedures followed by low yields make this process uneconomical. Industrially the large quantities of metal powder required make this process extremely difficult to handle on a large scale, whilst the specific metal required must be chosen with care as to prevent conversion of the parent functional group to another functionality.

Presently industry is dominated by difunctional phenyl derivatives through either one or two base nuclei. No difunctional furan derivatives through two base nuclei are presently synthesised on an industrial scale, Considering 5,5'diformyl-2,2'difuran it has been found that this compound has been synthesised through an Ullmann condensation utilising 5-iodo-2-furaldehyde, palladium catalysed coupling of 2-furaldehyde, or via the photolytic dimerisation of 5-bromo-2-furfural. The reported syntheses of the target compound involve labrious preparation of the starting materials, numerous work-up steps, high cost and low yields, It is an object of the present invention to prepare 5,5'-diformyl-2,2'-difuran and derivatives thereof in good yield and purity, and to avoid the use of high temperatures, solid metal powders and tedious work-up procedures.

BRIEF DESCRIPTION OF THE DRAWING

The single drawing FIGURE shows a continuous system for carrying out the method of the present invention.

DISCLOSURE OF THE INVENTION

Figure 1:
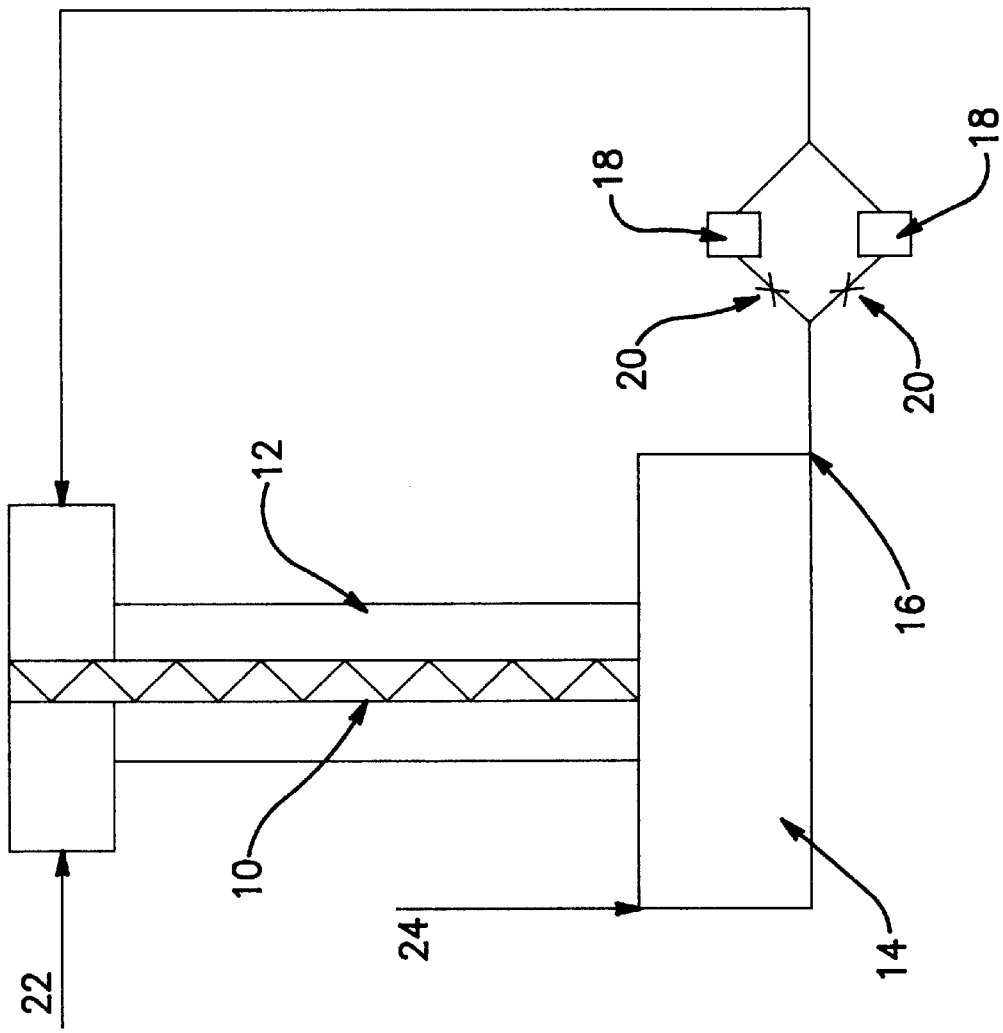

According to the invention a method of synthesising 5,5'-diformyl-2.2'-difuran and derivatives thereof includes the step of photochemical irradiating furfural with 5-bromo-2-furfural in the presence of a suitable acid scavenger; or with 5,5'-diformyl-2,2'-difuran and derivatives thereof with or without an acid scavenger, and recovering the 5,5'-diformyl-2,2'-difuran and derivatives thereof from the reaction mixture.

In a preferred form of the invention the acid scavenger is polyvinyl pyridine but it is expected that other acid scavengers may also be useful.

The solvent for the reactant is preferably acetonitrile but it is expected that other solvents may also be useful. However, petroleum ether, hexane, and dicholoromethane were found to give inferior yields. A yield of 87 percent has been obtained using acetonitrile as solvent.

The reaction mixture should be freed of oxygen prior to the photochemical irradiation and this way conveniently be achieved by purging it with nitrogen.

A UV lamp of wavelengths of the order of 200–400 nm may be used for the irradiation step.

It has been found that the 5-bromo-2-furfural may be used in very small or catalytic quantities. It has also been found that once sufficient 5,5'-diformyl-2,2'-difuran is in solution the reaction proceeds without further addition of 5-bromo-2-furfural and the process can be made continuous by constant addition of furfural and harvesting the precipitated 5,5'-diformyl-2,2'-difuran.

EXAMPLE 5-bromo-2-furfural (1) (0.181 G, 1.04 mmol) and furfural (2) 2.0 g, 20.8 mmol) dissolved in acetonitrile (400 ml) contained in a quartz flask was treated with activated polyvinyl pyridine (0,4 g, 25 mmol). The solution was purged with nitrogen for 15 minutes and then irradiated with a UV lamp (400 w medium to high pressure mercury lamp) for 25 h. The solution was treated with charcoal (ca. 2 g) and warmed at 75° C. with stirring for 5 minutes, filtered hot, concentrated under reduced pressure to a small volume (ca. 20 ml) and cooled to 0° C. for 20 minutes to afford pure 5,5'diformyl-2,2'-difuran product or the reacted mixture was poured into an excess of diethyl ether resulting in rapid precipitation of 5,5'diformyl-2,2'-difuran (3) in quantitative yield.

In another example of the invention the reacted solution is led to a holding tank where a degree of crystallisation occurs. This is then passed to a filter for removal of the crystals and then supernatant liquid is returned to the irradiation zone. Unreacted liquid may be fed to the irradiation zone or to the holding tank to maintain a predetermined volume of liquid in the continuous system.

In the single drawing FIGURE, a continuous system is shown comprising a UV lamp (10) surrounded by a sleeve (12) for the furfural and 5-bromo-2-furfural solution to pass and be irradiated. The irradiated liquid passes into a holding tank (14) from which it is withdrawn at low level (16). From there it is passed to a filtering station comprising alternative filters (18) controlled by valves (20). The supernatant liquid is returned to the irradiation zone. Unreacted solution and additional raw feed material may be added at 22 or 24 to maintain a predetermined volume of reactants in the system whilst 5,5'diformyl-2,2' difuran is continuously harvested (filtered) from the reaction mixture at the filter station.

The diformyl compound may be converted by ordinary chemical routes to various derivatives, of which the following have been prepared.

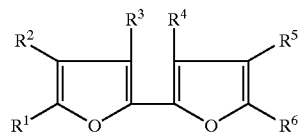

$R^1=R^6=CO_2H$; $R^2=R^3=R^4=R^5=H$: 5,5' Dicarboxylic acid -2,2'-difuran (m.p>300° C.).
$R^1=R^6=CH_2OH$; $R^2=R^3=R^4=R^5=H$: 5,5'-Dimethylacohol-2,2'-difuran m.p.136° C.).
$R^1=R^6=CH=CH-C-Ph$; $R^2=R^3=R^4=R^5=H$:
where Ph=phenyl
Bis-5,5'-(3-oxo-3-phenyl-1-propenyl-2,2'difuran (m.p. 232° C.).

$$R^1=R^6=CH=CH-\overset{O}{\overset{\|}{C}}-CH_3;$$

$R^2=R^3R^4=R^5=H$: 5,5'-di(but-1-ene-3-one)-2,2'difuran (m.p. 168° C.).
$R^1=R^6=CH=N-Ph$; $R^2=R^3=R^4=R^5=H$: 5-Formyl-5'-N-pentamethylene-2,2'-difuran.

$$R^1=R^6=\overset{O}{\overset{\|}{C}}-NH_2;$$

$R^2=R^3=R^4=R^5=H$: 5,5'-Diamido-2,2'-difuran (m.p. 180° C.).
$R^1=R^6=CH_2NH_2$; $R^2=R^3=R^4=R^5=H$: 5,5'-Diaminomethyl-2,2'-difuran
$R^1=R^6=CH=CH_2$; $R^2=R^3=R^4=R^5=H$: 5,5'-Divinyl-2,2'-difuran.

$$R^1=R^6=CH\overset{O}{\overset{/\backslash}{-}}CH;$$

$R^2=R^3=R^4=R^5=H$: 5,5'-Dioxiranyl-2,2'-difuran.
$R^1=R^6=CH=NOH$; $R^2=R^3=R^4=R^5$ H: 5,5'-(Dioxime)-2,2'-difuran.
$R^1=R^6=C\equiv N$, $R^2=R^3=R^4=R^5=H$ 5,5 Dinitrilo-2,2'-difuran.
$R^1=R^6=CH(OAc)_2$; $R^2=R^3=R^4=R^5=H$ 5,5'-Bis(diacetate)-2,2'-difuran m.p. 153–154° C.
$R^1=R^6=CH=CHNO_2$; $R^2=R^3=R^4=R^5=H$ 5,5'-Di(nitrovinyl)-2,2'difuran.
$R^1=R^6=CH=CHCO_2H$; $R^2=R^3=R^4=R^5=H$ 5,5'-Diacrylic acid-2,2'-difuran.

What is claimed is:

1. A method of synthesizing 5,5'-diformyl-2,2'-difuran and derivatives thereof, comprising the steps of subjecting a reaction mixture of furfural or a derivative thereof to photochemical irradiation with a halogenated furfural in the presence of an acid scavenger, and harvesting produced 5,5'-diformyl-2,2'-difuran and derivatives.

2. The method according to claim 1 in which the halogenated furfural is present in catalytic amounts only, the 5,5'-diformyl-2,2'-difuran produced being sufficient to react with said furfural or derivative thereof.

3. The method of claim 1 in which the halogenated furfural is 5-bromo-2-furfural.

4. The method according to claim 1 in which the acid scavenger is polyvinyl pyridine.

5. The method of claim 1 in which the photochemical irradiation is carried out in acetonitrile as a solvent.

6. The method according to claim 1 in which the reaction mixture is purged of oxygen prior to the irradiation.

7. The method of claim 1, wherein said 5,5'-diformyl-2,2'-difuran is produced continuously by the periodic addition of further furfural.

8. The method according to claim 1 in which the produced 5,5'-diformyl-2,2'-difuran and derivatives include:

$R^1=R^6=CO_2H$; $R^2=R^3=R^4=R^5=H$: 5,5'-Dicarboxylic acid-2,2'-difuran, with a melting point >300° C.
$R^1=R^6=CH_2OH$; $R^2=R^3=R^4=R^5=H$: 5,5'-Dimethylacohol-2,2'-difuran, with a melting point of 136° C., $$R^1=R^6=CH=CH-\overset{O}{\overset{\|}{C}}-Ph;$$

$R^2=R^3=R^4=R^5=H$:
where Ph=phenyl
Bis-5,5'-(3-oxo-3-phenyl-1-propenyl)-2,2'-difuran, with a melting point of 232° C., $$R^1=R^6=CH=CH-\overset{O}{\overset{\|}{C}}-CH_3;$$

$R^2=R^3=R^4=R^5=H$: 5,5'-di(but-1-ene-3-one)-2,2'-difuran, with a melting point of 168° C.,
$R^1=R^6=CH=N-Ph$; $R^2=R^3=R^4=R^5=H$: 5-Formyl-5'-N-phenylmethylene-2,2'-difuran, $$R^1=R^6=\overset{O}{\overset{\|}{C}}-NH_2;$$

$R^2=R^3=R^4=R^5=H$: 5,5'-Diamido-2,2'-difuran, with a melting point of 180° C.,
$R^1=R^6=CH_2NH_2$; $R^2=R^3=R^4=R^5=H$: 5,5'-Diaminomethyl-2,2'-difuran,
$R^1=R^6=CH=CH_2$; $R^2=R^3=R^4=R^5=H$: 5,5'-Divinyl-2,2'-difuran, $$R^1=R^6=CH\overset{O}{\overset{/\backslash}{-}}CH;$$

$R^2=R^3=R^4=R^5=H$: 5,5'-Dioxiranyl-2,2'-difuran,
$R^1=R^6=CH=NOH$; $R^2=R^3=R^4=R^5=H$: 5,5'-(Dioxime)-2,2'-difuran,
$R^1=R^6=C\equiv N$; $R^2=R^3=R^4=R^5=H$: 5,5'Dinitrilo-2,2'-difuran,
$R^1=R^6=CH(OAc)_2$; $R^2=R^3=R^4=R^5=H$: 5,5'-Bis(diacetate)-2,2'-difuran, with a melting point of 153° C. or 154° C.,
$R^1=R^6=CH=CHNO_2$; $R^2=R^3=R^4=R^5=H$: 5,5'-Di(nitrovinyl)-2,2'-difuran, and
$R^1=R^6=CH=CHCO_2H$; $R^2=R^3=R^4=R^5=H$: 5,5'-Diacrylic acid-2,2'-difuran.

* * * * *